United States Patent [19]

Dunwell et al.

[11] 4,025,636

[45] May 24, 1977

[54] 2-(OPTIONALLY SUBSTITUTED)PHENYL-5 OR 6-SUBSTITUTED BENZOXAZOLES

[75] Inventors: David William Dunwell, Camberley; Delme Evans, Peter; Terence Alan Hicks, Farnborough, all of England

[73] Assignee: Lilly Industries, Ltd., London, England

[22] Filed: Feb. 4, 1976

[21] Appl. No.: 655,669

Related U.S. Application Data

[63] Continuation-in-part of Ser. No. 515,132, Oct. 16, 1974, abandoned.

[30] Foreign Application Priority Data

Oct. 23, 1973 United Kingdom ............. 49258/73

[52] U.S. Cl. ........................... 424/269; 260/307 D; 424/272

[51] Int. Cl.$^2$ ..................................... C07D 263/56
[58] Field of Search ............... 260/307 D; 424/269, 424/272

[56] References Cited

OTHER PUBLICATIONS

Dunwell et al., C.A. 82, 118774b (1975) Abstract of J. Med. Chem., 1975, 18(1), pp. 53–58.

*Primary Examiner*—Raymond V. Rush
*Attorney, Agent, or Firm*—James L. Rowe; Everet F. Smith

[57] ABSTRACT

2-(Optionally substituted)phenyl-benzoxazoles having a carboxy alkyl, a tetrazolyl, or oxazolinyl group at the 5 or 6 position useful as aspirin-like non-steroidal, non-narcotic, analgesic, antipyretic and anti-inflammatory agents.

4 Claims, No Drawings

2-(OPTIONALLY SUBSTITUTED)PHENYL-5 OR 6-SUBSTITUTED BENZOXAZOLES

CROSS-REFERENCE

This application is a continuation-in-part of our co-pending application Ser. No. 515,132 filed Oct. 16, 1974, now abandoned.

This invention relates to heterocyclic chemical compounds and more particularly to certain novel derivatives of benzoxazole which are pharmacologically active and/or which may be used as chemical intermediates in preparing compounds possessing pharmacological activity.

The scope of the invention extends to processes for preparing the compounds of the invention, to pharmaceutical compositions containing the pharmacologically-active compounds, and to methods of treatment comprising administration of an effective dose of the active compounds or of pharmaceutical compositions comprising the active compounds.

According to the present invention there are provided novel benzoxazole derivatives of the formula:

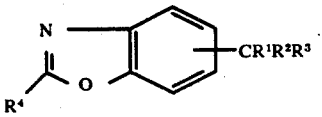

wherein the group $-CR^1R^2R^3$ is in the 5- or 6-position of the benzoxazole nucleus, $R^4$ is a phenyl group optionally substituted in one or two available positions by one or more $C_{1-6}$ alkylsulphonyl, halogen, $C_{1-6}$ alkyl, $C_{1-6}$ alkoxy, $C_{1-6}$ haloalkyl, nitro, $C_{2-7}$ acyl, hydroxy, amino, $C_{1-6}$ alkylamino, or $C_{2-7}$ acylamino or optionally substituted in two adjacent positions by methylene- or ethylene-dioxy, $R^3$ is one of the groups:

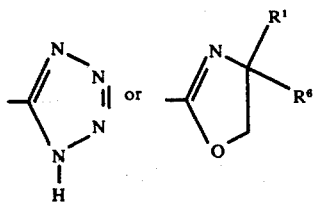

where $R^5$ and $R^6$ are independently hydrogen, $C_{1-6}$ alkyl or $C_{1-6}$ hydroxyalkyl, and $R^1$ and $R^2$ are independently hydrogen or $C_{1-6}$ alkyl; or $R^3$ is a nitrile group, carboxy or a salt, ester, amide or hydroxamic acid derivative thereof, or hydroxymethyl or an ester thereof, $R^1$ is hydrogen, halogen or $C_{1-6}$ alkyl, and $R^2$ is halogen, hydroxy, amino, $C_{1-6}$ alkoxy, $C_{2-7}$ acylamino or N-$C_{1-6}$ alkyl $C_{2-7}$ acylamino.

Benzoxazole derivatives of this invention can be represented by the formula:

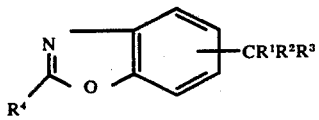

wherein the group $-CR^1R^2R^3$ is in the 5- or 6-position of the benzoxazole nucleus, $R^4$ is phenyl, methylphenyl, methoxyphenyl, chlorophenyl, fluorophenyl, or dichlorophenyl; $R^3$ is one of the groups:

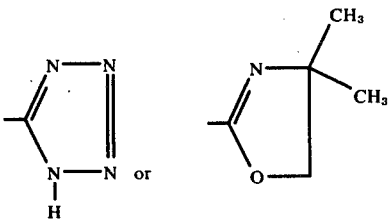

and $R^1$ and $R^2$ are independently hydrogen or methyl; or $R^3$ is carboxy or methyl or ethyl ester thereof, $R^1$ is hydrogen, chloro, bromo or methyl, and $R^2$ is chloro, bromo, hydroxy, methoxy, or acetoxy.

The present invention also provides a process for preparing the foregoing compounds of Formula I which comprises cyclizing a compound of the formula:

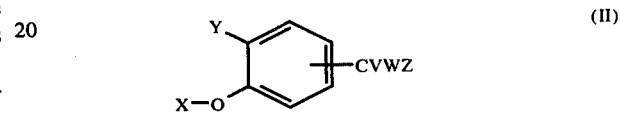

wherein V, W and Z are respectively the groups $R^1$, $R^2$ and $R^3$ or, independently, may be groups which are respectively convertible to the groups $R^1$, $R^2$ and $R^3$, and either X is hydrogen or the group $R^4$ CO— and Y is $H_2N$— or X is hydrogen and Y is the group $R^4$ CO—NH— or $R^4$ CH=N—, the cyclisation being carried out, in the case where X is hydrogen and Y is $H_2N$—; in the presence of a cyclising agent capable of donating the required group $R^4$ and thereafter where one or more of the groups V, W and Z in the resultant compound are not the same as groups $R^1$, $R^2$ and $R^3$, respectively, the said groups are converted to the groups. $R^1$, $R^2$ and $R^3$ in conventional manner.

In carrying out the foregoing cyclisation using a compound of formula II in which X is hydrogen and Y is $H_2N$—, it will be appreciated that, if one or more of the groups V, W and Z are also capable of reacting with the cyclising agent used, the reaction may produce a mixture of products rather than the desired compound of formula I alone. Although the undesired products could be separated from the reaction mixture, it is obviously desirable to use a compound of formula II in which V, W and Z are groups which are incapable of reaction with the cyclising agent. Thus, for example, in the case where Z is a group convertible to $R^3$, Z is preferably hydrogen or halogen and where Z is one of the groups encompassed by $R^3$, it is preferably a nitrile group or an esterified carboxy, esterified hydroxymethyl, carboxyamide or salified carboxy group.

The cyclisation of a compound of formula II in which X is hydrogen and Y is $R^4$ CO—NH— or in which X is $R^4$ CO— and Y is $H_2N$— may be carried out under the influence of heat and/or under acidic conditions, for example in the presence of hydrochloric acid or polyphosphoric acid. In the case where X is hydrogen and Y is $R^4$ CH=N—, cyclisation is easily accomplished by treatment with an oxidising agent such as lead tetraacetate or nickel peroxide.

When a compound of formula II in which X is hydrogen and Y is $H_2N$— is used, cyclisation is normally accomplished by mixing the cyclising agent with the compound of formula II, usually in a suitable solvent which may be water or an organic solvent such as pyridine, at room temperature or below followed by the application of heat to complete the reaction. Examples of suitable cyclising agents which may be used are componds of the formulae $R^4$ COOH, $(R^4 CO)_2O$, $R_4$ COCl, $R^4$ CONH$_2$, $R^4$ CONHNH$_2$, $R^4$ CN, $R^4$ C(OR$^7$)=NH and $R^4$ CCl=NR$^7$ where $R^7$ is $C_{1-4}$ alkyl.

As stated above, when one or more of the groups V, W and Z are not the groups $R^1$, $R^2$ and $R^3$ respectively, completion of the cyclisation step must be followed by conversion to the desired groups $R^1$, $R^2$ and/or $R^3$. As is well known in the art, many different types of groups may be converted to the $R^1$, $R^2$ and $R^3$ functions in the desired compounds of this invention. However, it is preferred for the purposes of the present invention that, where Z is not the group $R^3$, it is hydrogen or halogen. When Z is hydrogen, the compound resulting from the cyclisation reaction may be halogenated in conventional manner, for example using chlorine, sulphurylchloride, bromine or N-bromosuccinimide, preferably in the presence of a suitable solvent such as carbon tetrachloride, to produce the corresponding compound in which Z is halogen. This compound, or the same compound obtained directly from the above cyclisation reaction, may then be reacted with an alkali metal cyanide in a suitable diluent or solvent, usually under the influence of heat, to produce a compound of formula I in which $R^3$ is CN.

The latter compound, or the same compound obtained directly from the above cyclisation reaction, may then be treated in a number of ways to achieve its conversion to another compound of formula I. For example, the nitrile may then be reacted with ammonium azide, which is preferably formed in situ in the reaction medium, to produce a compound of the present invention wherein $R^3$ is a tetrazolyl group. Alternatively the nitrile may be reacted with an appropriate alcohol under acidic conditions to produce a compound of formula I in which $R^3$ is an esterified carboxy group. Alternatively, the nitrile can be hydrolysed, for example using sulphuric acid, to produce a compound of formula I in which $R^3$ is a carboxyamide group. Hydrolysis of the nitrile, or the last mentioned carboxyamide, with a strong base or an acid such as concentrated hydrochloric acid results in the formation of a compound of formula I in which $R^3$ is a carboxy group. This compound may be reacted with ethanolamine or an alkyl or hydroxyalkyl derivative thereof to produce a compound of the invention in which $R^3$ is an oxazolinyl or substituted oxazolinyl group. A resultant compound of formula I in which $R^3$ is esterified carboxy may be converted to a hydroxamic acid derivative by reaction with hydroxylamine. A resultant acid of formula I, i.e., where $R^3$ is a carboxy group or an ester thereof may readily be reduced, for example using diborane or a complex metal hydride, to yield the corresponding compound of formula I in which $R^3$ is hydroxymethyl and the alcohol resulting therefrom may then be esterified in conventional manner, for example by reaction with an appropriate carboxylic acid such as a $C_{2-4}$ alkanoic acid.

An acid of formula I may be salified by treatment with an appropriate base such as an ammonium, alkylammonium, aralkylammonium, aluminium, alkali metal or alkaline earth metal hydroxide and of course a salt of formula I may readily be converted to the free acid by treatment with an acid such as hydrochloric or sulphuric acid. An acid of formula I or a salt thereof may be converted to an ester by treatment with an appropriate alcohol or by treatment with a halide of the appropriate ester moiety or a salt of that halide if the ester moiety contains a basic nitrogen atom. An ester of formula I may of course be hydrolysed to the corresponding acid or alcohol of formula I by treatment with a suitable hydrolytic agent such as an inorganic base or acid. An acid of formula I or an ester thereof may also be converted to an amide of formula I by reaction with ammonia or an appropriate primary or secondary amine.

A resultant compound of formula I in which $R^1$ and/or $R^2$ is hydrogen may be alkylated to produce the corresponding compound of formula I in which $R^1$ and/or $R^2$ is $C_{1-16}$ alkyl. The alkylation may be carried out by interaction of an alkali metal derivative of the appropriate benzoxazole derivative with an alkyl halide such as, for example, methyl or ethyl iodide.

Compounds of formula I in which $R^1$ is hydrogen or halogen and $R^2$ is halogen may, for example, be prepared by reaction of the corresponding compounds in which $R^1$ and $R^2$ both represent hydrogen with an appropriate halogenating agent, for example N-bromosuccinimide. Compounds of formula I in which $R^1$ is hydrogen and $R^2$ is halogen may thereafter, for example, be reacted with an alcohol to produce the corresponding compound in which $R^2$ is alkoxy or may be hydrolysed to the corresponding hydroxy compound. Compounds of formula I in which $R^2$ is alkylamino may, for example, be prepared from the corresponding compound of formula I in which $R^2$ is hydrogen, when $R^3$ is, for example, a nitrile group, by reaction with the corresponding amine. The hydroxy and amino derivatives may subsequently be acylated. In the case of the amino derivatives either monoacyl or diacyl derivatives may be made.

In a situation where it may prove difficult by the above route to produce a compound of formula I in which both the group $R^4$ and the group —CR$^1$R$^2$R$^3$ have the desired meanings, a compound of formula I in which group $R^4$ is not the desired group may be prepared, the oxazole ring is the resultant compound is then cleaved in such a way as to regenerate a compound of formula II in which X is hydrogen and Y is H$_2$N—, for example by cleavage with concentrated hydrochloric acid at a temperature of around 150° C., and the resultant compound of formula II is re-cyclised in the presence of a cyclising agent which will donate the required group $R^4$.

Compounds of formula I in which $R^1$ is hydrogen or $C_{1-6}$ alkyl, $R^2$ is halogen, hydroxy, or $C_{2-7}$ acyloxy and $R^3$ is a nitrile group, carboxy or a salt, ester, amide or hydroxamic acid derivative thereof, or hydroxymethyl or an ester thereof, are useful intermediates not only in the preparation of pharmaceutically active compounds of formula I as defined herein but also in the preparation of the 2-phenyl benzoxazole derivatives described and claimed in Belgian Pat. No. 799,790. These latter 2-phenylbenzoxazoles can be prepared by hydrogenation of the intermediate compounds of formula I, where $R^2$ is halogen, hydroxy or $C_{2-7}$ acyloxy, using for example, a group VIII metal such as palladium as a catalyst.

It will be understood the scope of the invention extends not only to an overall process for preparing the novel compounds of the invention as described hereinbefore but also to the individual synthetic steps as herein described, and combinations of two or more of such synthetic steps.

Compounds of formula I have shown to have low toxicity and to possess an aspirin-like pharmacological activity, i.e., they can act as analgesic, antipyretic and- /or anti-inflammatory agents in mammals depending on whether the mammals to be treated have one or more of the aforesaid conditions; or as stated above have been found useful as intermediates in the preparation of such compounds.

The foregoing activities have been demonstrated in tests carried out in animals usually at doses of from 0.1 to 250 mg/kg. In the treatment of humans, the dose administered may be, for example, between 0.1 and 25 mg./kg. but, of course, doses outside this range may be used at the discretion of the physician treating the patient. The pharmacologically active compounds of formula I may be administered by the enteral or parenteral routes and for this purpose they will normally be formulated into pharmaceutical compositions comprising the active ingredient in association with at least one pharmaceutically acceptable carrier therefor. Such compositions form a part of this invention and will normally consist of the active ingredient mixed with a carrier, or diluted by a carrier, or enclosed or encapsulated by a carrier in the form of a capsule, sachet, cachet or other container. The carrier may be a solid, semi-solid or liquid material which serves as a vehicle, excipient, coating agent, or medium for the active ingredient. Some examples of the carriers which may be used are lactose, dextrose, sucrose, sorbitol, mannitol, starch, gum acacia, calcium phosphate, liquid paraffin, cocoa butter, oil of theobroma, alginates, tragacanth, gelatin, methyl cellulose, polyoxyethylene sorbitan monolaurate, methyl- or propyl-hydroxybenzoate, ethyl cellulose acetate phthalate, low viscosity acetyl cellulose acetate, paraffin wax, mineral wax, vegetable wax, vegetable gum, silicone rubbers such as liquid polydimethylsiloxane rubber, plasticised or unplasticised polyvinyl chloride, plasticised polyethylene terephthalate, modified collagen, cross-linked hydrophilic polyether gel, cross-linked polyvinyl alcohol or cross-linked partially hydrolysed polyvinyl acetate.

Advantageously the compositions of the invention are formulated in a dosage unit form containing from 1 to 1000 mg. (preferably 25 to 500 mg.) of the active ingredient. Examples of suitable dosage unit forms are tablets, hard or soft gelatin capsules, microcapsules and suppositories as well as drug dispensing systems comprising the active ingredient contained in a flexible, imperforate polymeric material through which the drug may be released slowly by diffusion. More generally, the term "dosage unit form" as used herein means a physically discrete unit containing the active ingredient, generally in admixture with and/or enclosed by a pharmaceutical carrier, the quantity of active ingredient being such that one or more units are normally required for a single therapeutic administration.

In addition to the active ingredient of formula I, the compositions of the present invention may also contain one or more pharmacologically active ingredients, for example, acetylsalicyclic acid and salts thereof, caffeine, codeine phosphate, phenylbutazone, paracetamol, dextropropoxyphene and indomethacin.

The compositions of the present invention will of course be adapted to the particular route of administration. Thus, for oral administration, tablets, pills, capsules, solutions or suspensions may be used; for parenteral administration, sterile injection solutions or suspensions may be used; for rectal administration, suppositories may be used; and for topical administration, creams, lotions or ointments may be used. Any of the foregoing compositions may, of course, be formulated in delayed or sustained release form in a manner well known in the art.

Examples of the novel benzoxazole derivatives of the present invention are as follows:

2-p-Chlorophenyl-5-[1'-(5''-tetrazolyl)ethyl]benzoxazole;

2-p-Chlorophenyl-5-[1'-(4'',4''-dimethyl-2''-oxazolin-2''-yl)ethyl]benzoxazole;

Ethyl 2-bromo-2-(p-chlorophenyl-5-benzoxazolyl)acetate;

Ethyl 2,2-dibromo-2-(p-chlorophenyl-5-benzoxazolyl)acetate;

Methyl 2-methoxy-2-(p-chlorophenyl-5-benzoxazolyl)acetate;

2-Methylamino-2-(2-p-chlorophenyl-5-benzoxazolyl)propionitrile;

2-Methylamino-2-(2-p-chlorophenyl-5benzoxazolyl)propionic acid;

N-Acetyl-2-methylamino-2-(2-p-chlorophenyl-5-benzoxazole)propionic acid;

2-Hydroxy-2-(2-p-chlorophenyl-5-benzoxazolyl)propionic acid, and the corresponding 6-benzoxazolyl compounds. The following examples further illustrate the invention.

EXAMPLE 1 a.

2-p-Chlorophenyl-5-[1'-(5''-tetrazolyl)ethyl]benzoxazole p-Chlorobenzoyl chloride (33.25 g; 0.19 mole) was added with cooling during 20 minutes to a stirred solution of 2-(3-amino-4-hydroxyphenyl)propionitrile (28.35 g; 0.175 mole) in dry pyridine (200 ml.) at 0°–3° C. After addition was complete the mixture was heated at 100° C. for one hour. It was then evaporated under reduced pressure to yield crude 2-(3-p-chlorobenzamido-4-hydroxyphenyl)propionitrile as an oil. The oil was boiled for 30 minutes during which time the temperature of the vapour above the oil rose to 130° C. On cooling the residue solidified. Recrystallisation of the solid from methanol yielded 2-(2'-p-chlorophenyl-5'-benzoxazolyl)propionitrile (29.00 g.) m.p. 150°–153° C.

Analysis: Calculated: C, 67.96; H, 3.92; N, 9.90; Found: C, 67.57; H, 3.96; N, 9.25.

A mixture of 2-(2'-p-chlorophenyl-5'-benzoxazolyl)propionitrile (5.1 g.), sodium azide (1.31 g.), ammonium chloride (1.08 g.) and dimethylformamide (20 ml.) was heated at 125° C. for 24 hours. The mixture was evaporated to dryness and the residue was stirred with water. The solid was filtered off and was recrystallised from ethanol. This yielded the tetrazole derivative 2.4 g., m.pt. 232°–234° C.

Analysis: Found: C, 59.2; H, 4.0; N, 21.4; Cl, 11.2; [$C_{16}H_{12}N_5OCl$] requires C, 59.0; H, 3.7; N, 21.5; Cl, 10.9%]

Similarly prepared were:

b. 2-p-Fluorophenyl-5-[1'-(5''-tetrazolyl)ethyl]benzoxazole c. 2-(2,4-dichlorophenyl)-5-[1'-(5''-tetrazolyl)ethyl]benzoxazole d. 2-p-Methylphenyl-5-[1'-(5''-tetrazolyl)ethyl]benzoxazole e. 2-p-Methoxyphenyl-5-[1'-(5''-tetrazolyl)ethyl]benzoxazole f. 2-phenyl-5-[1'-(5''-tetrazolyl)ethyl]benzoxazole.

The microanalytical analysis of the compounds (b) to (f) was in full accord with the expected theoretical values.

EXAMPLE 2

2-p-Chlorophenyl-5-[1'-(4'',4''-dimethyl-2''-oxazolin-2''-yl)ethyl-]benzoxazole

A solution of 2'-(2'-p-chlorophenyl-5'-benzoxazolyl)propionitrile (prepared as described in Example 1) (28.3 g; 0.1 mole) in concentrated hydrochloric acid (220 ml.) was refluxed for 2.5 hours. The mixture was poured into ice/water (1 liter). The precipitated 2-(2'-p-chlorophenyl-5'-benzoxazolyl)propionic acid was filtered off and washed with water. The dry acid weighed 25 g.

Analysis: C, 63.68; H, 4.00; N, 4.64; Found: C, 63.50; H, 4.16; N, 4.72.

A mixture of 2-(2'-p-chlorophenyl-5'-benzoxazolyl)-propionic acid (3.5 gm.), (2-amino-2-methylpropanol (1.3 ml.) and xylene (70 ml.) was heated using a Dean and Stark apparatus to collect the water formed. After 24 hours, the solution was evaporated to dryness and the residue was crystallised from toluene to yield the title compound.

Similarly prepared were:
b. 2-phenyl-5-[1'-(4'',4''-dimethyl-2''-oxazolin-2''-yl)ethyl]benzoxazole.
c. 2-(2,4-dichlorophenyl)-5-[1'-(4'',4''-dimethyl-2''-oxazolin-2''-yl)ethyl]benzoxazole.
d. 2-p-fluorophenyl-5-[1'-(4'',4''-dimethyl-2''-oxazolin-2''-yl)ethyl]benzoxazole.
e. 2-p-methylphenyl-5-[1'-(4'',4''-dimethyl-2''-oxazolin-2''-yl)ethyl]benzoxazole.
f. 2-p-methoxyphenyl-5-[1'-(4'',4''-dimethyl-2''-oxazolin-2''-yl)ethyl]benzoxazole.

The compounds in Examples (b) to (f) above were characterised by a combination of thin-layer chromatography and C,H,N microanalysis.

EXAMPLE 3 a. Ethyl 2-bromo-2-(p-chlorophenyl-5-benzoxazolyl)acetate

A suspension of p-chloro-benzimidoethyl ether hydrochloride (16.5 g) and 3-amino-4-hydroxyphenyl acetic acid (12.53 g) in methanol (75 ml.) were refluxed for 2 hours. After standing at room temperature overnight the white solid product was removed by filtration. Recrystallisation from ethanol gave 2-(p-chlorophenyl)-5-benzoxazolylacetic acid, m.p. 241°–242° C.

Analysis: Calculated: C, 62.61; H, 3.50; N, 4.86, Found: C, 62.89; H, 3.59; N, 4.92.

A suspension of 2-(p-chlorophenyl)-5-benzoxazolylacetic acid (26 g.) and p-toluene sulphonic acid (4.6 g.) in dry benzene (156 ml.) and dry absolute ethanol (78 ml.) was refluxed for 38 hours. Evaporation gave a solid which was dissolved in ethyl acetate (2 l) and washed with an aqueous saturated sodium bicarbonate solution (6 × 50 ml.). Evaporation of the organic phase gave ethyl 2-(2-p-chlorophenyl-5-benzoxazolyl)acetate as a solid (24.1 g.); m.pt. 133° C.

A suspension of ethyl 2-(2-p-chlorophenyl-5-benzoxazolyl)acetate (19.68 g.), N-bromosuccinimide (10 g.) and α-azoisobutyronitrile (approx. 20 mg.) in dry carbon tetrachloride (300 ml.) was refluxed under ultra violet light (Hanovia lamp model 16) for 29 hours. After cooling to room temperature, the mixture was filtered. The filtrate was evaporated to leave a gum (27.4 g.) which solidified. NMR evidence indicated the presence of approximately 10% molar ethyl 2-bromo-(2-p-chlorophenyl-5-benzoxazolyl) acetate. A suspension of this crude bromo compound (3.87 g.), N-bromosuccinimide (0.15 g.) and α-azoisobutyronitrile (approx. 20 mg.) in dry carbon tetrachloride (50 ml.) was refluxed under U.V. light for a further 21 hours. After cooling the reaction mixture to room temperature and removing undissolved solids by filtration, the carbon tetrachloride solution was evaporated to leave a brown oil, which subsequently solidified. This solid was twice recrystallised from ethanol to yield a buff coloured solid (2.4 g.), m.p. 81°–82° C.

Analysis: $C_{17}H_{10}BrClNO_3$ Calculated: C, 51.73; H, 3.31; N, 3.54; Br, 20.25 Found: C, 51.45; H, 3.29; N, 3.50; Br, 20.46.

Similarly prepared and characterised were:
b. Ethyl 2-bromo-2-(phenyl-5-benzoxazolyl)acetate.
c. Ethyl 2-bromo-2-(p-fluorophenyl-5-benzoxazolyl)acetate.
d. Ethyl 2-bromo-2-(2,4-dichlorophenyl-5-benzoxazolyl)acetate,
e. Ethyl 2-bromo-2-(p-methoxyphenyl-5-benzoxazolyl)acetate.
f. Ethyl 2-bromo-2-(p-methylphenyl-5-benzoxazolyl)acetate

EXAMPLE 4 a. Ethyl 2,2-dibromo-2-(p-chlorophenyl-5-benzoxazolyl) acetate

The bromo compound (3.16 g.) from Example 3 was suspended together with N-bromosuccinimide (2.86 g.) and α-azoisobutyronitrile (approx. 20 mg.) in dry carbon tetrachloride (4.5 ml.) and refluxed under U.V. light for 66 hours. After cooling to room temperature and filtering to remove undissolved solids, the carbon tetrachloride solution was evaporated to leave a gum which solidified. The NMR spectrum of the solid showed that it was the required product.

Similarly prepared and characterised were:
b. Ethyl 2,2-dibromo-2-(phenyl-5-benzoxazolyl)acetate.
c. Ethyl 2,2-dibromo-2-(p-fluorophenyl-5-benzoxazolyl)acetate.
d. Ethyl 2,2-dibromo-2-(2,4-dichlorophenyl-5-benzoxazolyl)acetate.
e. Ethyl 2,2-dibromo-2-(p-methoxyphenyl-5-benzoxazolyl)acetate.
f. Ethyl 2,2-dibromo-2-(p-methylphenyl-5-benzoxazolyl)acetate

EXAMPLE 5 a. Methyl 2-methoxy-2-(p-chlorophenyl-5-benzoxazolyl)acetate

Sodium (0.23 g.) was dissolved in dry methanol (60 ml.) and this solution added to ethyl 2-bromo-2-(p-chlorophenyl-5-benzoxazolyl)acetate (2.8 g.). The resulting solution was stirred for 68 hours at room temperature and then evaporated at 20° C. in vacuo to leave a residual oil. The oil was stirred in water (50 ml.) and the pH adjusted to 4 by the addition of glacial acetic acid. The resulting suspension was extracted with ether (3 × 75 ml.). The extracts were combined and washed with saturated sodium bisulphite solution (3 × 25 ml.). After drying ($Na_2SO_4$), the ether solution was evaporated to leave a gummy solid (2.15 g.). 1 Gram was purified by chromatography to yield a waxy solid (0.4 g.), which was subsequently recrystallised from carbon tetrachloride and 40°-60° petroleum ether. The resulting solid was the required product, m.p. 100°-105° C.

Similarly prepared and characterised by C, H and N microanalysis were:
  b. Methyl 2-methoxy-2-(phenyl-5-benzoxazolyl)acetate
  c. Methyl 2-ethoxy-2-(p-fluorophenyl-5-benzoxazolyl)acetate
  d. Methyl 2-methoxy-2-(2,4-dichlorophenyl-5-benzoxazolyl)acetate
  e. Methyl 2-methoxy-2-(p-methoxyphenyl-5-benzoxazolyl)acetate
  f. Methyl 2-methoxy-2-(p-methylphenyl-5-benzoxazolyl)acetate

EXAMPLE 6 a.

2-Methylamino-2-(2-p-chlorophenyl-5-benzoxazolyl)-propionitrile 2-(2'-p-Chlorophenyl-5-benzoxazolyl)propionitrile (5 g.) and a 33% solution of methylamine in ethanol (50 ml.) under reflux for 24 hours gave the expected methylamino compound as an oil. The structure of this product was confirmed by thin-layer chromatography.

The following nitriles were similarly prepared and characterised by thin-layer chromatography.
  b. 2-Methylamino-2-(2-p-fluorophenyl-5-benzoxazolyl)propionitrile.
  c. 2-Methylamino-2-(2-phenyl-5-benzoxazolyl)propionitrile
  d. 2-Methylamino-2-[2-(2,4-dichlorophenyl)-5-benzoxazolyl]propionitrile

EXAMPLE 7 a.

2-Methylamino-2-(2-p-chlorophenyl-5-benzoxazolyl)-propionic acid

The nitrile of Example 6(a) (2.0 g.) and concentrated hydrochloric acid (20 ml.) were heated under reflux for 3 hours. The cooled solution was treated with 50% NaOH solution until the pH was 5. This yielded the expected acid which was pure by thin layer chromatography.

Similarly, the following acids were prepared by hydrolysis of the nitriles formed in Examples 6(b) to (d) and characterised by thin-layer chromatogrphy.
  b. 2-Methylamino-2-(2-p-fluorophenyl-5-benzoxazolyl)propionic acid.
  c. 2-Methylamino-2-(2-phenyl-5-benzoxazolyl)propionic acid.
  d. 2-Methylamino-2-[2-(2,4-dichlorophenyl)-5-benzoxazolyl]propionic acid.

EXAMPLE 8 a.

N-Acetyl-2-methylamino-2-(2-p-chlorophenyl-5-benzoxazolyl)propionic acid

The acid (1 g.) of Example 7(a) and acetic anhydride (10 ml.) were heated under reflux for 1 hour and the excess of anhydride was evaporated under reduced pressure. Recrystallisation of the solid from ethanol gave the required N-acetyl compound. Thin-layer chromatography was in agreement with the expected structure.

Similarly, the following N-acylated compounds were prepared and characterised by C, H and N microanalysis:
  b. N-acetyl-2-methylamino-2-(2-p-fluorophenyl-5-benzoxazolyl)propionic acid.
  c. N-acetyl-2-methylamino-2-(2-phenyl-5-benzoxazolyl)propionic acid.
  d. N-acetyl-2-methylamino-2-[2-(2,4-dichlorophenyl)-5-benzoxazolyl]propionic acid.

EXAMPLE 9 a.

2-Hydroxy-2-(2-p-chlorophenyl-5-benzoxazolyl)acetic acid

Reaction of ethyl 2-bromo-2(p-chlorophenyl-5-benzoxazolyl)acetate with sodium hydroxide solution gave the expected hydroxy-acid. Formation of the final product was confirmed by thin-layer chromatography.

Similarly, the following 2-hydroxy-compounds were prepared and characterised:
  b. 2-hydroxy-2-(2-p-fluorophenyl-5-benzoxazolyl)acetic acid.
  c. 2-hydroxy-2-(2-p-chlorophenyl-5-benzoxazolyl)-propionic acid
  d. 2-hydroxy-2-[2-(2,4-dichlorophenyl)-5-benzoxazolyl]propionic acid
  e. 2-hydroxy-2-(2-phenyl-5-benzoxazolyl)propionic acid.
  f. 2-hydroxy-2-(2-phenyl-5-benzoxazolyl)acetic acid.
  g. 2-hydroxy-2-[2-(2,4-dichlorophenyl)-5-benzoxazolyl]propionic acid.

EXAMPLE 10 a. 2-p-chlorophenyl-6-benzoxazolylcarboxaldehyde cyanohydrin

A suspension of N-bromosuccinimide (40 g.) in a solution of 2-p-chlorophenyl-6-methylbenzoxazole (50 g.) in carbon tetrachloride (65 ml.) was heated under reflux in the presence of U.V. radiation, for 2 hours. The solution was filtered and evaporated to dryness. The residue was crystallised from carbon tetrachloride to give 2-p-chlorophenyl-6-benxozazolyl-ethyl bromide A mixture of this compound (65 g.), hexamine (20 g.), acetic acid (250 ml.) and water (250 ml.) was heated under reflux for 3 hours. Concentrated hydrochloric acid (250 ml.) was added and refluxing continued for 1 hour. After cooling, the solid was filtered off and recrystallised to give 2-p-chlorophenyl-6-benzoxazolylcarboxaldehyde, m.pt. 153° C.

Analysis: Found: C, 65.6; H, 3.2; N, 5.6; Cl, 14.0, $C_{14}H_8ClNO_2$ requires: C, 65.3; H 3.1; N, 5.4; Cl, 13.8%.

A saturated solution of sodium metabisulphite in water (27.5 ml.) was steadily added to a stirred suspension of 2-p-chlorophenyl-6-benzoxazolylcarboxaldehyde (25 g.) in a solution of sodium cyanide (5 g.) in water (200 ml). After stirring for three hours the solid was filtered off and recrystallised from ethyl acetate to yield 2-p-chlorophenyl-6-benzoxazolylcarboxaldehyde cyanohydrin, m.p. 178° C.

Analysis: Found; C, 63.3; H, 3.4; N, 9.6; Cl, 12.7, $C_{15}H_9ClN_2O_2$ requires: C, 63.3; H, 3.2; N, 9.8; Cl, 12.5%. Similarly, the following cyanohydrins were prepared and characterised by C, H, N microanalysis:

b. 2-p-fluorophenyl-6-benzoxazolylcarboxaldehyde cyanohydrin.
c. 2-p-chlorophenyl-5-benzoxazolylcarboxaldehyde cyanohydrin.
d. 2-phenyl-5-benzoxazolylcarboxaldehyde cyanohydrin.
e. 2-(2,4-dichlorophenyl)-5-benzoxazolylcarboxaldehyde cyanohydrin.

EXAMPLE 11 a. 2-p-Chlorophenyl-6-benzoxazolylglycolic acid

A solution of 2-p-chlorophenyl-6-benzoxazolylcarboxaldehyde cyanohydrin (20 g.) in concentrated hydrochloric acid (200 ml.) was heated on a steam bath for 1 hour. The solid produced on dilution with water was crystallised from acetic acid to give 2-p-chlorophenyl-6-benzoxazolylglycolic acid, m.p. 222°–4° C.

Analysis: Found; C, 59.6; H, 3.6; N, 4.7; Cl, 12.0 $C_{15}H_{10}ClNO_4$ requires, C, 59.3; H, 3.3; N, 4.6; Cl, 11.7%.

The cyanohydrins of Examples 10(b) to (e) were similarly hydrolysed to yield:
b. 2-p-fluorophenyl-6-benzoxazolylglycolic acid.
c. 2-p-chlorophenyl-5-benzoxazolylglycolic acid.
d. 2-phenyl-5-benzoxazolylglycolic acid.
e. 2-(2,4-dichlorophenyl)-5-benzoxazolylglycolic acid.

C,H,N Microanalysis carried out on the above acids was in full agreement with their expected structures.

EXAMPLE 12 a. Methyl-2-p-chlorophenyl-α-methoxy-6-benzoxazolylacetate

A mixture of 2-p-chlorophenyl-6-benzoxazolylglycolic acid (4.4 g.), silver oxide (6.6g.) and methanol (60 ml.) was stirred for sixteen hours. The solution was filtered and evaporated to dryness. The residue was crystallised from carbon tetrachloride to yield methyl 2-p-chlorophenyl-α-methoxy-6-benzoxazolylacetate, m.p. 131°–2° C.

Analysis: Found, C, 61.3; H, 4.5; N, 4.1, Cl, 10.8. $C_{17}H_{14}ClNO_4$ requires C, 61.5; H, 4.3; N, 4.2; Cl, 10.7%.

Similarly prepared (and characterised by microanalysis) were the following α-methoxy compounds:
b. Methyl 2-p-chlorophenyl-α-methoxy-5-benzoxazolylacetate.
c. Methyl 2-(2,4-dichlorophenyl)-α-methoxy-5-benzoxazolylacetate.

EXAMPLE 13 a. 2-p-chlorophenyl-α-methoxy-6-benzoxazolylacetic acid

Methyl 2-p-chlorophenyl-α-methoxy-6-benzoxazolyl-acetate (4.0 g.) was dissolved in dioxan (50 ml.) and a solution of sodium hydroxide (0.7g) in water was added. The solution was stirred for three hours then evaporated to dryness. The residue was stirred with dilute hydrochloric acid for thirty minutes. The solid was filtered off and recrystallised from water-ethanol to give 2-p-chlorophenyl-α-methoxy-6-benzoxazolylacetic acid, m.pt. 164°–6° C.

Analysis: Found, C, 60.3; H, 3.9; N, 4.6; Cl, 11.0, $C_{16}H_{12}ClNO_4$ requires, C, 60.5; H, 3.8; N, 4.4; Cl, 11.2%.

Similarly, the esters of Examples 12(b) and (c) were hydrolysed to yield:
b. 2-p-chlorophenyl-α-methoxy-5-benzoxazolyl acetic acid.
c. 2-(2,4-dichlorophenyl)-α-methoxy-5-benzoxazolyl acetic acid.

Thin-layer chromatography was in full agreement with the expected structures of the acids.

EXAMPLE 14 a. 2-phenyl-5-Benzoxazolylacetic acid

A solution of α-hydroxy-2-phenyl-5-benzoxazolylacetonitrile (2 g.) in acetic acid (30 ml.) containing palladium or charcoal was hydrogenated for 4 hours. The catalyst was filtered off and the solution was evaporated to dryness. The residue was recrystallised to give pure 2-phenyl-5-benzoxazolylacetic acid m.p. 175° C.

Similarly prepared were the following acids:
b. 2-p-fluorophenyl-5-benzoxazolylacetic acid.
c. 2-(2,4-dichlorophenyl)-5-benzoxazolylacetic acid.
d. 2-p-chlorophenyl-6-benzoxazolyl acetic acid.

EXAMPLE 15 a. 2-p-Chlorophenyl-5-benzoxazolylacetic acid

A solution of methyl α-bromo-2-p-chlorophenyl-5-benzoxazolylacetate (3 g.) in dioxan (30 ml.) was treated with aqueous 2N sodium hydroxide solution. The mixture was acidified and crude α-bromo-2-p-chlorophenyl-5-benzoxazolylacetic acid was filtered off. This solid was dissolved in ethanol (30 ml.) and palladium on charcoal added. The solution as hydrogenated for 3 hours. The catalyst was removed and the solution was evaporated to dryness. The residue was crystallised to give 2-p-chlorophenyl-5-benzoxazolylacetic acid, m.p. 241°–242° C.

Similarly prepared were the following acids:
b. 2-p-chlorophenyl-6-benzoxazolyl acetic acid.
c. 2(2,4-dichlorophenyl)-5-benzoxazolylacetic acid.
2-p-fluorophenyl-5-benzoxazolylacetic acid.

EXAMPLE 16 a. α-Acetoxy-2-p-chlorophenyl-5-benzoxazolylacetic acid

A mixture of 2-p-chlorophenyl-5-benzoxazolyl-glycolic acid (4 g.) and acetyl chloride (50 ml.) was heated under reflux for 24 hours. The residue on evaporation was crystallised to give pure α-acetoxy-2-chlorophenyl-5-benzoxazolylacetic acid.

A solution of this compound (2.5 g.) in acetic acid (30 ml.) containing palladium on charcoal was hydrogenated for 2 hours. The catalyst was removed and the solution was evaporated to dryness. The residue was crystallised to give pure 2-p-chlorophenyl-5-benzoxazolylacetic acid m.p. 241°–2° C.

Similarly prepared were:
b. 2-phenyl-5-benzoxazolyl acetic acid m.p. 175° C.
c. 2-(2,4-dichlorophenyl)-5-benzoxazolyl acetic acid.
d. 2-(p-chlorophenyl-6-benzoxazolyl acetic acid.

We claim:
1. A benzoxazole of the formula:

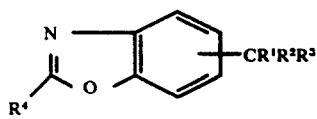

wherein the group —CR¹R²R³ is in the 5- or 6-position of the benzoxazole nucleus, R⁴ is phenyl, methylphenyl, methoxyphenyl, chlorophenyl, fluorophenyl, or dichlorophenyl; R³ is one of the groups:

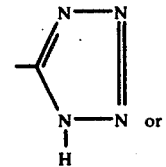 or 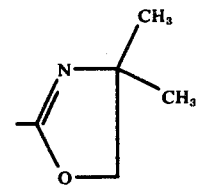

and R¹ and R² are independently hydrogen or methyl; or R³ is carboxy or methyl or ethyl ester thereof, R¹ is hydrogen, chloro, bromo, or methyl, and R² is chloro, bromo, hydroxy, methoxy, or acetoxy.

2. A compound of formula I as claimed in claim 1 wherein R³ is a carboxylic acid group.

3. A compound of formula I as claimed in claim 2 wherein R⁴ is phenyl or halo-substituted phenyl.

4. A pharmaceutical formulation comprising a chemotherapeutically effective amount of a pharmaceutically active compound of formula I as defined in claim 1 in association with at least one pharmaceutically acceptable carrier therefor.

* * * * *